(12) United States Patent
Dahlqvist et al.

(10) Patent No.: US 9,943,448 B2
(45) Date of Patent: Apr. 17, 2018

(54) METHOD FOR FORMING A WRAPPING SHEET HAVING IMPROVED SEALING

(71) Applicant: SCA HYGIENE PRODUCTS AB, Göteborg (SE)

(72) Inventors: Conny Dahlqvist, Göteborg (SE); Ulrika Persson, Göteborg (SE); Sofia Ekstedt, Göteborg (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 15/318,178

(22) PCT Filed: Jun. 13, 2014

(86) PCT No.: PCT/SE2014/050719
§ 371 (c)(1),
(2) Date: Dec. 12, 2016

(87) PCT Pub. No.: WO2015/190965
PCT Pub. Date: Dec. 17, 2015

(65) Prior Publication Data
US 2017/0128279 A1    May 11, 2017

(51) Int. Cl.
*A61F 13/15*    (2006.01)
*A61F 13/551*   (2006.01)
*A61F 13/84*    (2006.01)

(52) U.S. Cl.
CPC .. *A61F 13/15804* (2013.01); *A61F 13/15723* (2013.01); *A61F 13/15747* (2013.01);
(Continued)

(58) Field of Classification Search
CPC .................................................. A61F 13/5514
See application file for complete search history.

(56) References Cited

U.S. PATENT DOCUMENTS 3,913,580 A    10/1975  Ginocchio
3,957,569 A     5/1976  Freitag
(Continued)

FOREIGN PATENT DOCUMENTS

EP    0 368 914 A1    5/1990
EP    0 841 049 A1    5/1998
(Continued)

OTHER PUBLICATIONS

Office Action (Examination Report No. 1 for Standard Patent Application) dated Feb. 13, 2017, by the Australian Patent Office in corresponding Australian Patent Application No. 2014396900. (3 pages).
(Continued)

*Primary Examiner* — Carson Gross
*Assistant Examiner* — Marta S Dulko
(74) *Attorney, Agent, or Firm* — Buchanan Ingersoll & Rooney, PC

(57) ABSTRACT

A method for forming a wrapping material for hygiene articles involves: providing one of the inner edge portion and the outer edge portion of the edge zone of the first region with a first resealable adhesive, such that the other of the inner edge portion and the outer edge portion of the edge zone of the first region is adhesive-free; providing one of the inner edge portion and the outer edge portion of the edge zone of the second region with a first resealable adhesive, such that the other of the inner edge portion and the outer edge portion of the edge zone of the second region is adhesive-free; and providing at least one of the first central portion of the first region and the second central portion of the second region with a second adhesive; wherein the steps a-c are performed simultaneously.

18 Claims, 3 Drawing Sheets

(52) U.S. Cl.
CPC ...... *A61F 13/5514* (2013.01); *A61F 13/5515* (2013.01); *A61F 2013/8497* (2013.01)

(56) References Cited

U.S. PATENT DOCUMENTS

| | | | |
|---|---|---|---|
| 5,167,739 A | 12/1992 | Hutchinson et al. | |
| 5,238,178 A | 8/1993 | Hutchinson et al. | |
| 5,375,764 A | 12/1994 | Sauerwine | |
| H1454 H | 6/1995 | Cucuzza et al. | |
| 5,462,166 A | 10/1995 | Minton et al. | |
| 5,567,260 A | 10/1996 | McFall | |
| 5,569,230 A | 10/1996 | Fisher et al. | |
| 5,591,153 A | 1/1997 | Mattingly, III | |
| 5,598,970 A | 2/1997 | Mudry et al. | |
| 5,769,837 A | 6/1998 | Parr | |
| 5,792,131 A | 8/1998 | Mizutani | |
| 5,868,727 A | 2/1999 | Barr et al. | |
| 6,003,760 A | 12/1999 | Abercrombie | |
| 6,015,934 A | 1/2000 | Lee et al. | |
| 6,039,242 A | 3/2000 | Tee | |
| 6,176,850 B1 * | 1/2001 | Rosenfeld | A61F 13/476 604/385.04 |
| 6,203,512 B1 | 3/2001 | Farris et al. | |
| 6,234,229 B1 | 5/2001 | Tabuchi | |
| 6,322,106 B1 | 11/2001 | Mehta et al. | |
| 7,083,079 B2 | 8/2006 | Bethke | |
| 7,708,727 B2 * | 5/2010 | Woltman | A61F 13/5514 206/440 |
| 8,231,590 B2 | 7/2012 | Zander et al. | |
| 8,900,210 B2 | 12/2014 | Drevik et al. | |
| 2003/0163109 A1 | 8/2003 | Ohba et al. | |
| 2003/0225390 A1 | 12/2003 | Vogt et al. | |
| 2003/0234069 A1 | 12/2003 | Coenen et al. | |
| 2004/0107676 A1 | 6/2004 | Murray | |
| 2005/0137553 A1 | 6/2005 | Bechyne et al. | |
| 2005/0198931 A1 | 9/2005 | Cesiro et al. | |
| 2006/0025739 A1 | 2/2006 | DiPalma et al. | |
| 2006/0137568 A1 | 6/2006 | MacDonald et al. | |
| 2007/0049891 A1 | 3/2007 | Clark, Jr. et al. | |
| 2007/0189644 A1 | 8/2007 | Murray | |
| 2008/0067803 A1 | 3/2008 | Tanigawa | |
| 2009/0082747 A1 | 3/2009 | Carlen et al. | |
| 2010/0175825 A1 | 7/2010 | Baldauf | |
| 2010/0298797 A1 | 11/2010 | Ehlenbach et al. | |
| 2011/0028933 A1 | 2/2011 | Fung et al. | |
| 2011/0034897 A1 | 2/2011 | Nomoto et al. | |
| 2012/0090071 A1 | 4/2012 | Umebayashi | |
| 2012/0283682 A1 | 11/2012 | Otsubo et al. | |
| 2013/0165888 A1 * | 6/2013 | Kinoshita | A61F 13/5514 604/385.02 |
| 2013/0199956 A1 | 8/2013 | Hunter et al. | |
| 2014/0155852 A1 | 6/2014 | Nishimura et al. | |
| 2015/0112294 A1 | 4/2015 | Dahl et al. | |

FOREIGN PATENT DOCUMENTS

| | | |
|---|---|---|
| EP | 0 955 243 A2 | 11/1999 |
| EP | 2 589 356 A1 | 5/2013 |
| EP | 2 737 886 A1 | 6/2014 |
| GB | 2 273 279 A | 6/1994 |
| JP | 2003-199786 A | 7/2003 |
| JP | 2006-45417 A | 2/2006 |
| JP | 2009-73498 A | 4/2009 |
| JP | 2013-85818 A | 5/2013 |
| WO | WO 88/10219 A1 | 12/1988 |
| WO | WO 89/00459 A1 | 1/1989 |
| WO | WO 95/00092 A1 | 1/1995 |
| WO | WO 97/34556 A2 | 9/1997 |
| WO | WO 00/45767 A1 | 8/2000 |
| WO | WO 03/030796 A1 | 4/2003 |
| WO | WO 2005/087167 A1 | 9/2005 |
| WO | WO 2010/071512 A1 | 6/2010 |
| WO | WO 2010/135566 A1 | 11/2010 |
| WO | WO 2012/102071 A1 | 8/2012 |
| WO | WO 2012/157621 A1 | 11/2012 |
| WO | WO 2013/162430 A1 | 10/2013 |
| WO | WO 2014/188239 A1 | 11/2014 |

OTHER PUBLICATIONS

Ciba-Geigy AG (Durr's) Applications [1977] RPC 83. Published Feb. 17, 1977.
Section 2.9.2.8 of Australian Patent Manual of Practice & Procedure, titled "Printed Matter", Retrieved Feb. 19, 2017. <http://manuals.ipaustralia.gov.au/patents/national/patentable/2.9.2.8_printed_matter.htm>. (2 pages).
*Wikipedia, "Corona treatment", http://en.wikipedia.org/wiki/Corona_treatment, Mar. 16, 2015, 6 pages.
*International Search Report (PCT/ISA/210) dated Feb. 23, 2015, by the Swedish Patent Office as the International Searching Authority for International Application No. PCT/SE2014/050724.
*Written Opinion (PCT/ISA/237) dated Feb. 23, 2015, by the Swedish Patent Office as the International Searching Authority for International Application No. PCT/SE2014/050724.
*International Preliminary Report on Patentability (PCT/IPEA/409) dated Jun. 8, 2016, by the Swedish Patent Office as the International Searching Authority for International Application No. PCT/SE2014/050724.
*International Search Report (PCT/ISA/210) dated Feb. 20, 2015, by the Swedish Patent Office as the International Searching Authority for International Application No. PCT/SE2014/050725.
*Written Opinion (PCT/ISA/237) dated Feb. 20, 2015, by the Swedish Patent Office as the International Searching Authority for International Application No. PCT/SE2014/050725.
*International Preliminary Report on Patentability (PCT/IPEA/409) dated Jun. 13, 2016, by the Swedish Patent Office as the International Searching Authority for International Application No. PCT/SE2014/050725.
*International Search Report (PCT/ISA/210) dated Feb. 16, 2015, by the Swedish Patent Office as the International Searching Authority for International Application No. PCT/SE2014/050719.
*Written Opinion (PCT/ISA/237) dated Feb. 16, 2015, by the Swedish Patent Office as the International Searching Authority for International Application No. PCT/SE2014/050719.
*International Preliminary Report on Patentability (PCT/IPEA/409) dated Jun. 14, 2016, by the Swedish Patent Office as the International Searching Authority for International Application No. PCT/SE2014/050719.
*European Patent Office Letter dated Mar. 27, 2015, for International Application No. PCT/SE2014/050719.
*International Search Report (PCT/ISA/210) dated Feb. 11, 2015, by the Swedish Patent Office as the International Searching Authority for International Application No. PCT/SE2014/050720.
*Written Opinion (PCT/ISA/237) dated Feb. 11, 2015, by the Swedish Patent Office as the International Searching Authority for International Application No. PCT/SE2014/050720.
*Written Opinion of the International Preliminary Examining Authority (PCT/IPEA/408) dated Jun. 3, 2016, by the Swedish Patent Office as the International Searching Authority for International Application No. PCT/SE2014/050720.
*Written Opinion of the International Preliminary Examining Authority (PCT/IPEA/408) dated Jul. 7, 2016, by the Swedish Patent Office as the International Searching Authority for International Application No. PCT/SE2014/050720.
*European Patent Office Letter dated Aug. 24, 2015, for International Application No. PCT/SE2014/050720.
*European Patent Office Letter dated Jun. 29, 2016, for International Application No. PCT/SE2014/050720.
*International Search Report (PCT/ISA/210) dated Mar. 2, 2015, by the Swedish Patent Office as the International Searching Authority for International Application No. PCT/SE2014/050726.
*Written Opinion (PCT/ISA/237) dated Mar. 2, 2015, by the Swedish Patent Office as the International Searching Authority for International Application No. PCT/SE2014/050726.
*Written Opinion of the International Preliminary Examining Authority (PCT/IPEA/408) dated Jun. 3, 2016, by the Swedish

(56) References Cited

OTHER PUBLICATIONS

Patent Office as the International Searching Authority for International Application No. PCT/SE2014/050726.
*International Preliminary Report on Patentability (PCT/IPEA/409) dated Jul. 12, 2016, by the Swedish Patent Office as the International Searching Authority for International Application No. PCT/SE2014/050726.
*European Patent Office Letter dated Apr. 7, 2015, for International Application No. PCT/SE2014/050726.
*International Search Report (PCT/ISA/210) dated Feb. 11, 2015, by the Swedish Patent Office as the International Searching Authority for International Application No. PCT/SE2014/050718.
*International Preliminary Report on Patentability (PCT/IPEA/409) dated Jun. 8, 2016, by the Swedish Patent Office as the International Searching Authority for International Application No. PCT/SE2014/050718.
*European Patent Office Letter dated Mar. 27, 2015, for International Application No. PCT/SE2014/050718.

* cited by examiner

METHOD FOR FORMING A WRAPPING SHEET HAVING IMPROVED SEALING

TECHNICAL FIELD

The present disclosure relates to a method for forming a wrapping sheet for hygiene articles, wherein the wrapping sheet provides a tightly sealed package both when packaging a new and disposing of a used hygiene article.

BACKGROUND

Disposable hygiene articles, such as sanitary napkins and panty liners, are normally packaged individually in e.g. a single wrap or a quick wrap. A single wrap is formed from a sheet of material, such as a plastic film. In order to prevent the garment-affixing adhesive, provided on the garment-facing side of a hygiene article, from being caught by the single wrap material, the garment-affixing adhesive is usually protected by a release liner formed from a material having a low adhesive force to the garment-affixing adhesive. Before arranging the hygiene article in the garment, the user has to remove the single wrap material, and subsequently remove the release liner, thus exposing the garment-affixing adhesive. Using a single wrap has the disadvantage of introducing an additional step during handling of a hygiene article. In order to overcome this disadvantage, a quick wrap is offered, being a single wrap with a release paper permanently attached to it, for instance by means of a construction adhesive, which means that both the single wrap and the release liner are removed in one single step.

Individual packages facilitate hygienic carrying of single articles for future use, e.g. in a handbag. The edges of the individual packages are often sealed by means of ultrasonic welding or heat welding. Further, the packaging units are often used both as a means for packaging an unused article and for disposal of the used article.

It is desirable that used articles of this kind can be disposed of discretely and hygienically. This may be particularly important when the user lacks the possibility to dispose of the used article immediately after the used article has been replaced, e.g. when there is no waste bin available in the toilet area. In this case, the user may need to put the used article in e.g. her handbag or backpack, which requires the package to be adequately sealed in order to avoid staining and odour.

One solution addressing the disposal problem has been suggested in WO 2013/162430, describing a wrapping sheet being formed from a sheet having at least one folding axis dividing the sheet into a first region and a second region. The inner surface of the first region comprises an inner edge portion and an outer edge portion, wherein one of the portions is provided with adhesive, and the other of the portions is adhesive-free. Further, one of the inner and outer edge portions of the second region is either provided with adhesive or is adhesive-free in a complementary manner to the first region. Thus, when the sheet is folded about the folding axis, the edge portions carrying adhesive in the first region are brought in contact with the adhesive-free edge portions in the second region, and the edge portions carrying adhesive in the second region are brought in contact with the adhesive-free edge portions in the first region. The wrapping sheet disclosed in WO 2013/162430 provides an improved sealing both when packaging a new hygiene article, and when the wrapping sheet is used for disposal of a soiled hygiene article.

However, the manufacturing process of a wrapping sheet described in WO 2013/162430 may be adversely affected by the presence of adhesive zones. For instance, when the wrapping sheet of WO 2013/162430 is a quick wrap, the adhesive arranged at the edge portions of the wrapping sheet may have a negative impact on the step of arranging the release liner of the quick wrap.

Hence, there is a need for a method for forming a wrapping sheet which can be used both for packaging a new hygiene article and for hygienic keeping and disposal of the used hygiene article, which is aesthetically appealing and which facilitates manufacturing.

SUMMARY

The present disclosure provides a method for forming a wrapping sheet for hygiene articles which substantially eliminates the drawbacks of the methods for forming packaging units discussed above.

The present disclosure provides a method for forming a wrapping sheet providing a possibility of forming a tight package both for a new and a used article, thus keeping the new article sanitary and clean prior to use, and eliminating the risk of staining and odour when a used article is packaged. The wrapping sheet manufactured according to the method of the present disclosure is easy to unfold and reseal, is aesthetically appealing, and provides facilitated manufacturing.

As used herein, the term "inner surface" refers to the surface of the wrapping sheet facing the product positioned inside the packaging unit, and the term "outer surface" refers to the surface opposite to the inner surface, i.e. the surface facing the ambient.

By the term "edge zone" is meant the portion of the wrapping sheet adjacent to the edges of the packaging unit. The width of an edge zone may be varied.

The term "inner edge portion" refers to the portion of the edge zone positioned towards the centreline of the packaging unit.

The term "outer edge portion" refers to the portion of the edge zone positioned towards the edge of the packaging unit.

The term "central portion" refers to the portion of the wrapping sheet excluding the edge zone.

By the term "single ply" is meant a wrapping sheet comprising a single ply of a coherent material. The examples of a single ply wrapping sheet may be a plastic film, such as a polyethylene film, a nonwoven material, a metallic foil or the like. A single ply material may be a non-homogenous material such as a plastic film material comprising integrated layers or a nonwoven material having varying fibre composition in different parts of the material. A single ply material as used herein does not comprise materials having separable layers.

By the term "laminate" is meant a wrapping sheet comprising at least two united separable plies of material that can be the same or different. In the context of the present disclosure, the laminate may for example be constituted of two separable plies of plastic film, a film and nonwoven, two plies of nonwoven or the like.

By the term "permanently attached" is meant two surfaces being in such a contact with each other that it is not possible to break the contact without affecting either or both surfaces.

"Releasably affixed" means two surfaces being bonded to each other such that the bond may be readily broken without affecting the surfaces.

By the term "resealable adhesive" is meant an adhesive that provides a non-permanent adhesive bond between two adherent surfaces, i.e. a bond that may be broken by applying a pulling force to the adherent, and recreated by applying a pressing force to the adherent.

A method according to the present disclosure is suitable for forming a wrapping material for hygiene articles from a continuous web of wrapping sheets. Each wrapping sheet has an inner surface and an outer surface, wherein the inner surface comprises an edge zone comprising an inner edge portion and an outer edge portion. The wrapping sheet has at least one first folding axis dividing the wrapping sheet into a first region and a second region, wherein the first region comprises a first central portion, and the second region comprises a second central portion.

The method according to the present disclosure comprising the steps of:
a. providing one of the inner edge portion and the outer edge portion of the edge zone of the first region with a first resealable adhesive, such that the other of the inner edge portion and the outer edge portion of the edge zone of the first region is adhesive-free;
b. providing one of the inner edge portion and the outer edge portion of the edge zone of the second region with a first resealable adhesive, such that the other of the inner edge portion and the outer edge portion of the edge zone of the second region is adhesive-free in a complementary manner to the edge zone of the first region;
c. providing at least one of the first central portion of the first region and the second central portion of the second region with a second adhesive.

The steps a-c are performed simultaneously. In other words, the first resealable adhesive and the second adhesive are applied simultaneously as a single manufacturing step. This is a great advantage since the manufacturing process is facilitated, and the risk of the subsequent steps of the manufacturing sequence being affected by the presence of the first resealable adhesive at the edge zones is minimized.

The width of the adhesive-covered edge portions may be varied depending on the adhesive strength desired. The wider the adhesive-covered edge zones, the stronger the sealing. The width of the adhesive-covered edge portions may be same or different in the different regions.

Preferably, the length of the adhesive-covered edge portions in each region is equal to the length of each region. Also, the length of the adhesive-covered edge portions in each region may be shorter than the length of each region.

The entire first and/or second central portion may be provided with the second adhesive. Preferably, only a portion of the first and/or the second central portions is provided with the second adhesive. Such an embodiment has the advantage of minimizing the consumption of the second adhesive, and consequently the manufacturing costs. Further, if only a portion of the first and/or second central portion is provided with the second adhesive, the manufacturing is facilitated, since the risk of the second adhesive affecting the subsequent manufacturing steps is minimized.

The method according to the present disclosure may further comprise the steps of:
d. providing a release liner having a wrap-facing surface and a user-facing surface;
e. bringing the wrap-facing surface of the release liner in contact with the inner surface of the wrapping sheet such that at least a portion of the wrap-facing surface of the release liner becomes permanently attached to the inner surface of the wrapping sheet in at least the first and the second central portions being provided with the second adhesive by means of the second adhesive.

The release liner may be manufactured from any suitable material known to the person skilled in the art, such as paper, non-woven or plastic film material. Further, in order to provide a release liner that is easily detachable from the garment-affixing adhesive that may be present on the garment-facing surface of the hygiene article, the release liner may be silicone-coated on the user-facing surface of the release liner.

The release liner may have substantially the same shape as the hygiene article inside the packaging unit, or may have the shape being different from the shape of the hygiene article. The size of the release liner may vary. Preferably, the longitudinal extension of the release liner is 60-100% of the longitudinal extension of the wrap. The transverse extension of the release liner may be 30-90% of the transverse extension of the wrap.

The release liner may further comprise a print in the form of a text, a graphic, a symbol or a combination thereof. The print may be arranged on the user-facing surface of the release liner, on the wrap-facing surface of the release liner, or on both the user-facing surface and the wrap-facing surface of the release liner.

It is sufficient that a portion of the release liner is attached to a portion of the inner surface of the wrap to thereby be in contact therewith. Thus, only a portion of the release liner may be attached to the central portion of the inner surface of the wrap being provided with the second adhesive. Alternatively, the entire wrap-facing surface of the release liner may be attached to the inner surface of the wrapping sheet. Preferably, two or three portions of the release liner are attached to the inner surface of the wrap, wherein the portions of the wrap-facing surface of the release liner that are attached to the inner surface of the wrap are spaced apart along the longitudinal direction of the release liner. The release liner is permanently attached to the wrap by means of the second adhesive. The second adhesive may be of any type known to a person skilled in the art, such as a construction adhesive.

The method according to the present disclosure may further comprise the step of:
f. releasably affixing a hygiene article to the user-facing surface of the release liner.

The hygiene article may be releasably affixed to the release liner either by means of a third resealable adhesive or by any other suitable fastening means known to the person skilled in the art, e.g. hook-and-loop fastening means.

The hygiene article may be releasably affixed to the user-facing surface of the release liner after the release liner has been permanently attached to the inner surface of the wrapping sheet, i.e. step f occurs after step e. Alternatively, the hygiene article may be releasably affixed to the user-facing surface of the release liner before the release liner has been permanently attached to the inner surface of the wrapping sheet, i.e. step f occurs before step e.

As mentioned above, the hygiene article may be releasably affixed to the release liner by means of a third resealable adhesive. The method according to the present disclosure may thus further comprise the step of:
g. providing the user-facing surface of the release liner with a third resealable adhesive;
wherein step g occurs before step f.

After the hygiene article has been arranged on the release liner being permanently attached to the inner surface of the wrapping sheet, the wrapping sheet may be folded in order to form a tight package around the hygiene article. The method according to the present disclosure may further comprise the step of:

h. folding the wrapping sheet about the first folding axis such that the edge portions carrying the first resealable adhesive in the first region are brought in contact with the adhesive-free edge portions in the second region, and the edge portions carrying the first resealable adhesive in the second region are brought in contact with the adhesive-free edge portions at the first region.

The first resealable adhesive used with the wrapping sheet is one which has a very high self-adhesion but which can be readily separated or released from other materials, such as plastic materials or paper which has been treated with a release agent. As the adhesive-coated edge portions of the wrapping sheet of the present disclosure are not in contact with each other when the wrapping sheet is folded, the wrapping sheet can be readily opened and resealed, providing a tight disposal package. At the same time, the tensile strength of the adhesively sealed edges of the wrapping sheet using the adhesive pattern of the present disclosure is sufficient to provide a tight package for both a new and a used article, and low enough to provide a readily-opened package.

The geometrical shape of the wrapping sheet can vary depending on the type of the hygiene article to be packaged. The wrapping sheet may be circular, triangular, square, rectangular, or any other shape suitable for the hygiene article to be packaged. It is desirable, however, that the wrapping sheet has at least one symmetry axis.

As mentioned above, the wrapping sheet comprises at least one folding axis. The number of folding axes may vary depending on how the wrapping sheet is intended to be folded. It is preferred that the wrapping sheet comprises from one to three folding axes.

The prevailing shape of the wrapping sheet of material for forming a wrapping sheet is square or rectangular. Such a wrapping sheet according to the present disclosure has side edges, referred to herein as longitudinal edges, a first and a second transverse edge and corner portions, the edge zones of the first and second regions of the wrapping sheet of material being arranged along the longitudinal edges. The edge portions covered with the first resealable adhesive and adhesive-free portions are thus positioned along the longitudinal edges. Preferably, the resealable adhesive arranged at the outer edge portions is positioned such that it extends all the way to the longitudinal edges of the sheet.

The first transverse edge zone is provided at the transverse edge of the first region. The positioning of the second transverse edge zone depends on the number of folding axes. When the wrapping sheet comprises one folding axis, the second transverse edge zone is arranged at the transverse edge of the second region. When the wrapping sheet comprises two folding axes, the second transverse edge zone is arranged at the transverse edge of the third region, and so forth.

The wrapping sheet may have a first and a second folding axis dividing the sheet into the first region, the second region and a third region. In such an embodiment, the method according to the present disclosure may further comprise the steps of:

i. providing a portion of the edge zone of the third region with the first resealable adhesive;
j. folding the wrapping sheet about the second folding axis such that the inner surface of the third region is brought in contact with the outer surface of the first region.

Preferably, step i is performed simultaneously with steps a-c, i.e. the first resealable adhesive is applied to the edge portions of all three regions simultaneously with the second adhesive being applied to at least one central portion of the first and the second regions. Also, step i may occur after steps a-c, but before step d. The first resalable adhesive may be arranged in any of the inner and the outer edge portions of the third region.

Step j may be performed after step h, i.e. folding may be initiated around the first folding axis. If the first resealable adhesive is arranged in the edge portions of the third region being corresponding to the adhesive-carrying edge portion of the second region, the folding order may be reversed, i.e. step j may be performed before step h. Thus, the folding may be initiated around the second folding axis, bringing the portions carrying the first resealable adhesive in the third region in contact with the adhesive-free edge portions in the second region, and bringing the edge portions carrying the first resealable adhesive in the second region in contact with the adhesive-free edge portions at the third region.

The method according to the present disclosure may further comprise the step of:

k. providing at least one of the transverse edge zones of the wrapping sheet with the first resealable adhesive.

wherein step k is preferably performed simultaneously with the steps a-c.

Preferably, the first transverse edge zone of the first region of the wrapping sheet is provided with the first resealable adhesive, while the second transverse edge zone of the wrapping sheet is adhesive-free. When the wrapping sheet comprises one folding axis, it is conceivable that a portion of the first transverse edge zone of the first region is provided with the first resealable adhesive, while the remaining portion of the first transverse edge zone of the first region is adhesive-free, and a portion of the second transverse edge zone of the second region is provided with the first adhesive, while a remaining portion of the second transverse edge zone of the second region is adhesive-free in a complementary manner to the transverse edge zone of the first region. Thus, when the wrap is folded about the first folding axis, the transverse edge portion carrying the first resealable adhesive in the first region is brought in contact with the adhesive-free transverse edge portion in the second region, and the transverse edge portion carrying the first resealable adhesive in the second region is brought in contact with the adhesive-free transverse edge portion in the first region. Also, both the first and the second transverse edge zones of the wrapping sheet may be provided with the first resealable adhesive when the wrapping sheet comprises at least two folding axes.

In order to facilitate opening, at least one of the corner portions may be free from the first resealable adhesive such that a gripping tab is formed.

The first resealable adhesive and the third resealable adhesives may be pressure-sensitive adhesives, such as Lunatack® D656 BD 19 available from H. B. Fuller, and the second adhesive may be a construction adhesive.

The wrapping sheet and/or the release liner may be opaque and/or comprise print.

The wrapping sheet for forming a wrapping sheet may be a single ply sheet of any suitable material known to the person skilled in the art, such as polyethylene film or nonwoven. The wrapping sheet may also be a laminate comprising at least two distinct layers. Laminates suitable for packaging of hygiene articles are assumed to be known to the person skilled in the art, and are not in any way limiting for the present disclosure.

The wrapping sheet of material forming a wrapping sheet according to the present disclosure may comprise an odour-inhibiting or odour-neutralising substance. Such a substance may be applied in any suitable manner known to the person skilled in the art, e.g. as a coating, activatable microcapsules, impregnated patches or the like. Further, such a substance may be arranged on or in the user prompting device. Preferably, such a substance is integrated into the user prompting device in order to avoid the need for an additional material.

It is conceivable that the wrapping sheet for forming a wrapping sheet according to the present disclosure may be stretchable or expandable, which may be advantageous if the hygiene article is greatly deformed during use, and may thus be difficult to wrap without deforming the packaging unit.

DETAILED DESCRIPTION OF PREFERRED EMBODIMENTS

Figure 1:
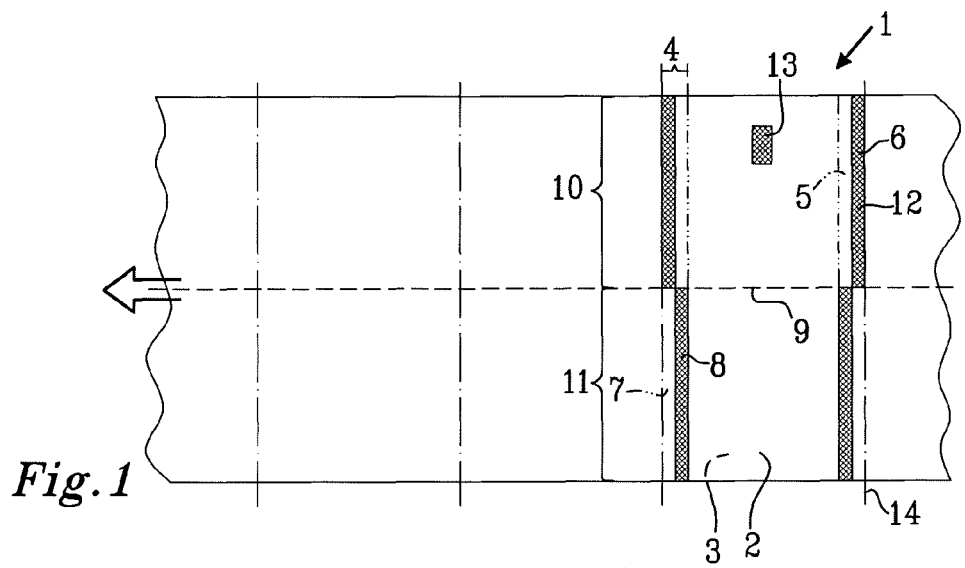
FIG. 1 depicts steps a-c of a method of an embodiment.
Figure 2:
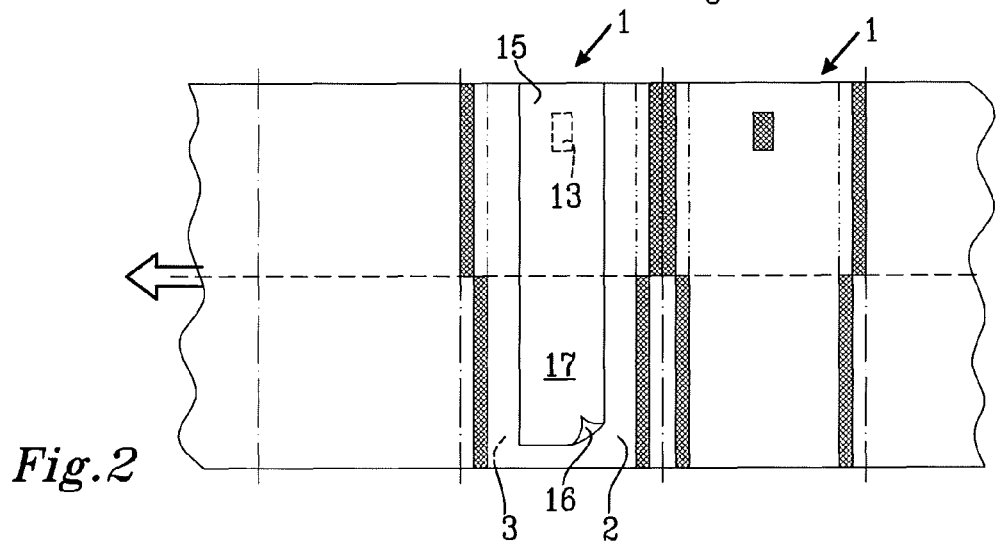
FIG. 2 illustrates steps d-e of the method of an embodiment.
Figure 3:
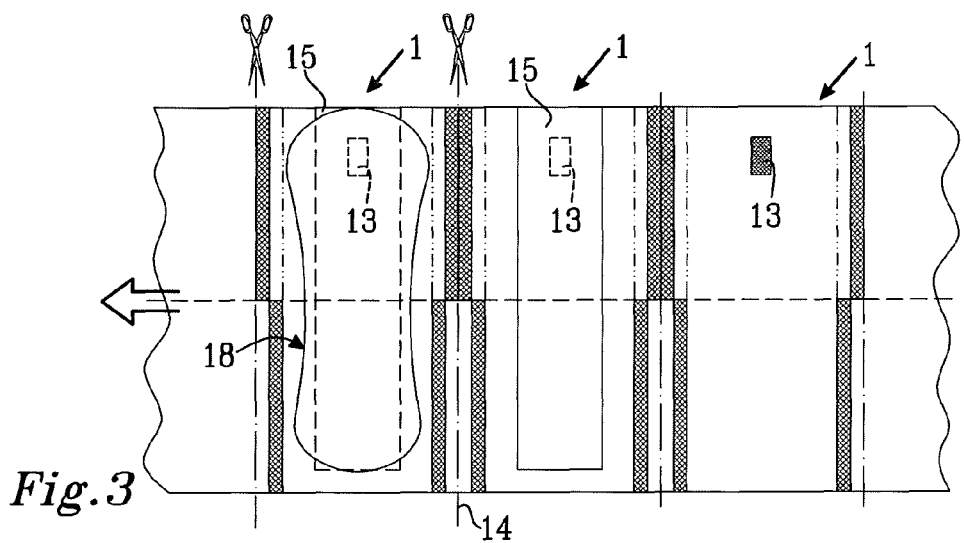
FIG. 3 shows step f of the method of an embodiment.

FIGS. 1-3 show one possible embodiment of the method according to the present disclosure. FIG. 1 depicts steps a-c of the method of the present disclosure for forming a wrapping material for hygiene articles from a continuous web of wrapping sheets. Each wrapping sheet 1 has an inner surface 2 and an outer surface 3, the inner surface comprising an edge zone 4 comprising an inner edge portion 5, 8 and an outer edge portion 6, 7. The wrapping sheet 1 has a first folding axis 9 dividing the wrapping sheet 1 into a first region 10 and a second region 11, wherein the first region 10 comprises a first central portion, and the second region 11 comprises a second central portion. According to the method of the present disclosure, the steps a-c performed simultaneously and shown in FIG. 1 are:
  a. providing the outer edge portion 6 of the edge zone of the first region 10 with a first resealable adhesive 12, such that the inner edge portion 5 of the edge zone of the first region 10 is adhesive-free;
  b. providing the inner edge portion 8 of the edge zone of the second region 11 with a first resealable adhesive 12, such that the outer edge portion 7 of the edge zone of the second region 11 is adhesive-free in a complementary manner to the edge zone of the first region 10;
  c. providing the first central portion of the first region 10 with a second adhesive 13.

The continuous web of wrapping sheets is then moved to the next step of the manufacturing sequence. According to FIG. 2, the next step in the manufacturing sequence is steps d and e, wherein, in step d, a release liner 15 is provided having a wrap-facing surface 16 and a user-facing surface 17. In step e, the wrap-facing surface 16 of the release liner 15 is brought in contact with the inner surface 2 of the wrapping sheet 1 such that a portion of the wrap-facing surface 16 of the release liner 15 becomes permanently attached to the inner surface 2 of the wrapping sheet 1 in the first central portions being provided with the second adhesive 13 by means of the second adhesive 13.

Further, a hygiene article 18 is releasably affixed to the user-facing surface 17 of the release line 15, according to step f of the method of the present disclosure (FIG. 3). The continuous web of the wrapping sheets is then folded according to step h of the method of the present disclosure about the folding axis 9 and cut along the cutting axes 14, thus forming tightly sealed individually wrapped hygiene articles (not shown).

Figure 4:
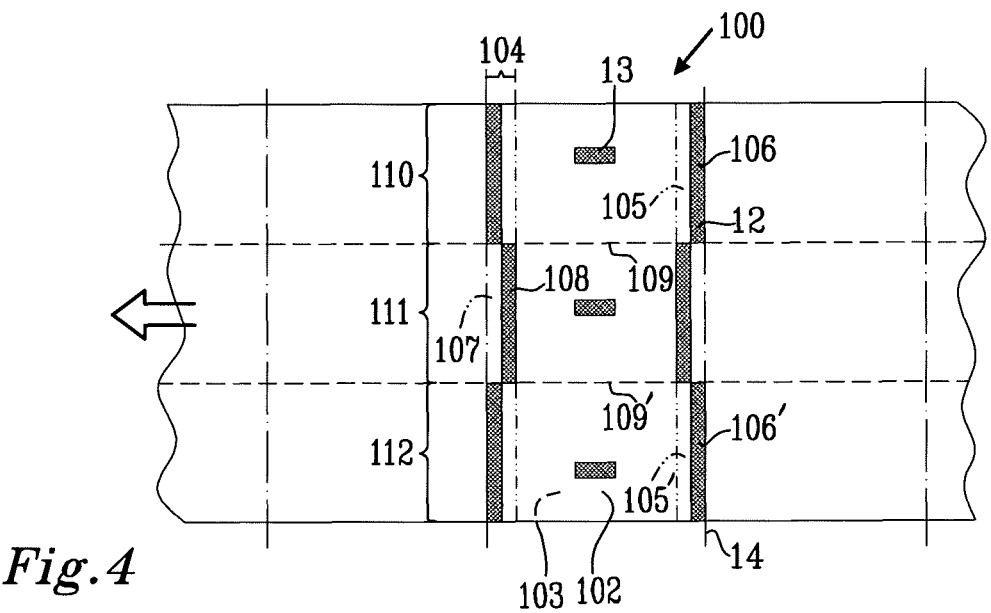
FIG. 4 depicts steps a-c and i of a method of an embodiment.
Figure 5:
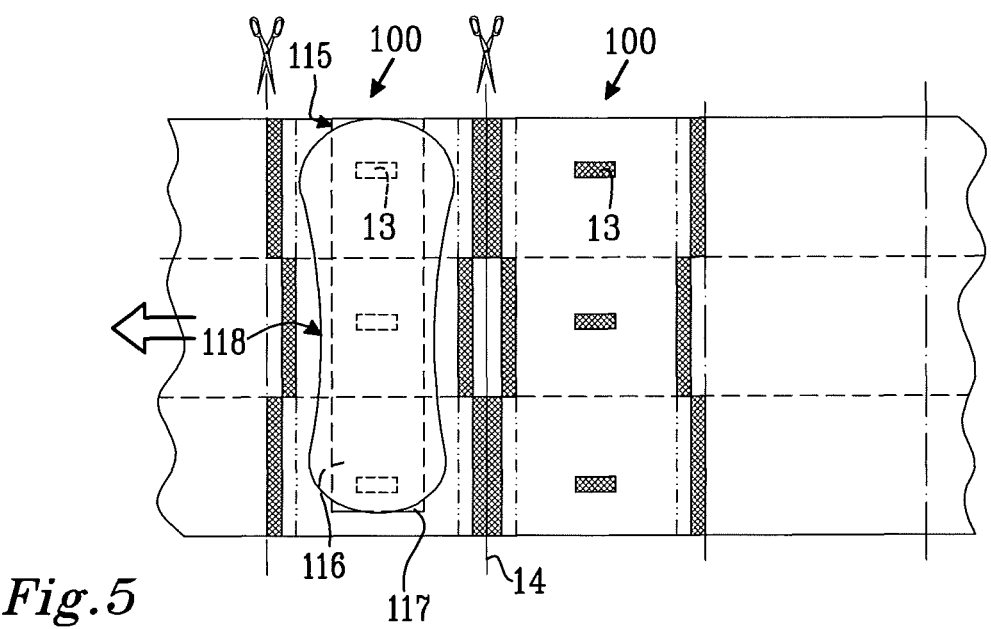
FIG. 5 illustrates steps e and f of the method of an embodiment, wherein step f occurs before step e.

An alternative embodiment of the method according to the present disclosure is illustrated in FIGS. 4 and 5. FIG. 4 depicts steps a-c and i of the method of the present disclosure, the steps performed simultaneously and being:
  a. providing the outer edge portion 106 of the edge zone of the first region 110 with a first resealable adhesive 12, such that the inner edge portion 105 of the edge zone of the first region 110 is adhesive-free;
  b. providing the inner edge portion 108 of the edge zone of the second region 111 with a first resealable adhesive 12, such that the outer edge portion 107 of the edge zone of the second region 111 is adhesive-free in a complementary manner to the edge zone of the first region 110;
  i. providing the outer edge portion 106' of the edge zone of the third region 112 corresponding to the adhesive-carrying outer edge portion 106 of the edge zone of the first region 110 with a first resealable adhesive 12, such that the inner edge portion 105' of the edge zone of the third region 112 is adhesive-free; and
  c. providing the central portions of the first region 110, the second region 111 and the third region 112 with a second adhesive 13.

The continuous web of wrapping sheets is then moved to the next step of the manufacturing sequence. According to FIG. 5, the next step in the manufacturing sequence is steps d-f, wherein step f is performed before step e. Thus, in step d, a release liner 115 is provided having a wrap-facing surface 116 and a user-facing surface 117. A hygiene article 118 is releasably affixed to the user-facing surface 117 of the release line 115, according to step f of the method of the present disclosure. The wrap-facing surface 116 of the release liner 115 is subsequently brought in contact with the inner surface 102 of the wrapping sheet 100 according to step e, such that a portion of the wrap-facing surface 116 of the release liner 115 becomes permanently attached to the inner surface 102 of the wrapping sheet 100 in the central portions being provided with the second adhesive 13 by means of the second adhesive 13.

Analogous to the above, the continuous web of the wrapping sheets is then folded according to steps h and j of the method of the present disclosure about the first folding axis 109 and the second folding axis 109', and cut along the cutting axes 14, thus forming tightly sealed individually wrapped hygiene articles (not shown).

Figure 6:
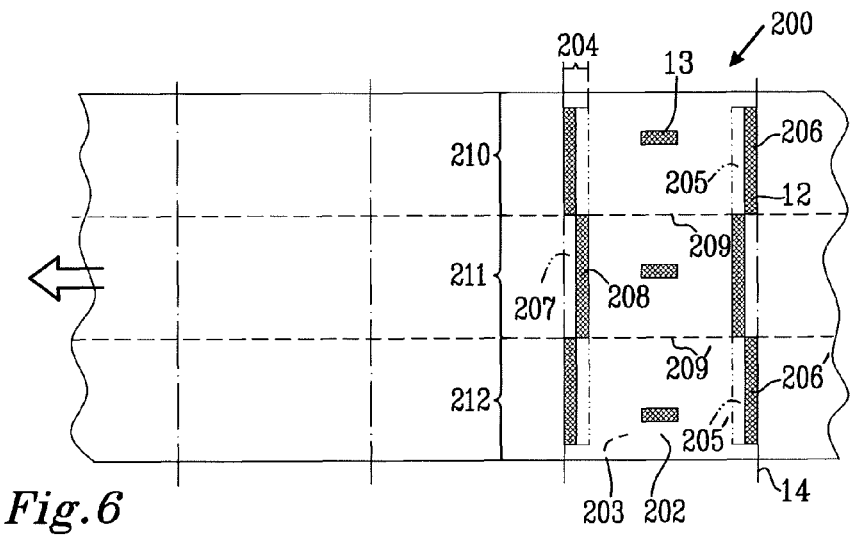
FIG. 6 shows steps a-c and i of a method of an embodiment.
Figure 7:
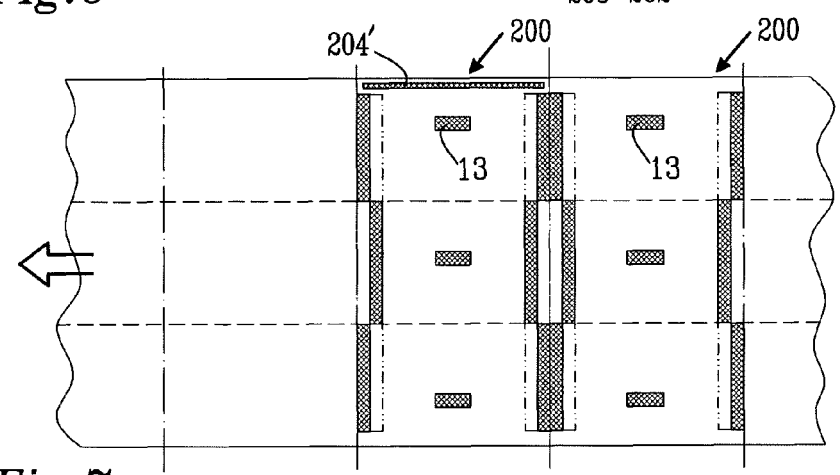
FIG. 7 depicts step k of the method of an embodiment.
Figure 8:
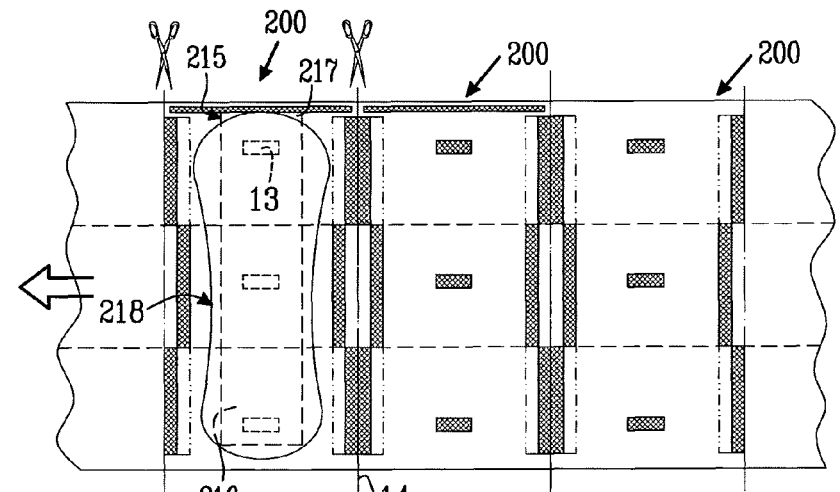
FIG. 8 illustrates steps e and f of the method of an embodiment, wherein step f occurs before step e.

Yet another embodiment of the method of the present disclosure is shown in FIGS. 6-8. FIG. 6 depicts steps a-c and i of the method of the present disclosure, the steps performed simultaneously and being:
  a. providing the outer edge portion 206 of the edge zone of the first region 210 with a first resealable adhesive 12, such that the inner edge portion 205 of the edge zone of the first region 210 is adhesive-free;

b. providing the inner edge portion 208 of the edge zone of the second region 211 with a first resealable adhesive 12, such that the outer edge portion 207 of the edge zone of the second region 211 is adhesive-free in a complementary manner to the edge zone of the first region 210;

i. providing the outer edge portion 206' of the edge zone of the third region 212 corresponding to the adhesive-carrying outer edge portion 206 of the edge zone of the first region 210 with a first resealable adhesive 12, such that the inner edge portion 205' of the edge zone of the third region 210 is adhesive-free; and c. providing the central portions of the first region 210, the second region 211 and the third region 212 with a second adhesive 13.

The continuous web of wrapping sheets 200 is then moved to the next step of the manufacturing sequence. According to FIG. 7, the next step of the manufacturing sequence according to the embodiment shown in FIGS. 6-8 is step k, i.e. providing the first transverse edge zone 204' of the wrapping sheet 200 with the first resealable adhesive 12. As mentioned above, step k. may be performed simultaneously with steps a-c.

According to FIG. 8, the subsequent step in the manufacturing sequence is steps d-f, wherein step f is performed before step e. Thus, in step d, a release liner 215 is provided having a wrap-facing surface 216 and a user-facing surface 217. A hygiene article 218 is releasably affixed to the user-facing surface 217 of the release line 215, according to step f of the method of the present disclosure. The wrap-facing surface 216 of the release liner 215 is subsequently brought in contact with the inner surface 202 of the wrapping sheet 200 according to step e of the method of the present disclosure, such that a portion of the wrap-facing surface 216 of the release liner 215 becomes permanently attached to the inner surface 202 of the wrapping sheet 200 in the central portions being provided with the second adhesive 13 by means of the second adhesive 13.

Analogous to the above, the continuous web of the wrapping sheets is then folded according to steps h and j of the method of the present disclosure about the first folding axis 209 and the second folding axis 209', and cut along the cutting axes 14, thus forming tightly sealed individually wrapped hygiene articles (not shown).

Although the present disclosure has been described with reference to various embodiments, those skilled in the art will recognise that changes may be made without departing from the scope of the disclosure. It is intended that the detailed description be regarded as illustrative and that the appended claims including all the equivalents are intended to define the scope of the present disclosure.

The invention claimed is:

1. A method for forming a wrapping material for hygiene articles from a continuous web of wrapping sheets, each wrapping sheet having an inner surface and an outer surface, said inner surface comprising a first edge zone comprising an inner edge portion and an outer edge portion, each wrapping sheet having at least one first folding axis, said at least one first folding axis dividing said wrapping sheet into a first region and a second region, wherein said first region comprises a first central portion, and said second region comprises a second central portion;

said method comprising the steps of:
a. providing one of said inner edge portion and said outer edge portion of said first edge zone of said first region with a first resealable adhesive, such that the other of said inner edge portion and said outer edge portion of said first edge zone of said first region is adhesive-free;

b. providing one of said inner edge portion and said outer edge portion of said first edge zone of said second region with a first resealable adhesive, such that the other of said inner edge portion and said outer edge portion of said edge zone of said second region is adhesive-free in a complementary manner to said first edge zone of said first region;

c. providing at least one of said first central portion of said first region and said second central portion of said second region with a second adhesive;

d. providing a release liner having a wrap-facing surface and a user-facing surface; and e. bringing said wrap-facing surface of said release liner in contact with said inner surface of said wrapping sheet such that at least a portion of said wrap-facing surface of said release liner becomes permanently attached to said inner surface of said wrapping sheet in said at least one of said first central portion and said second central portion provided with said second adhesive by means of said second adhesive;

f. folding said wrapping sheet about said at least one first folding axis such that said inner edge portion and said outer edge portion carrying said first resealable adhesive in said first region are brought in contact with said adhesive-free edge portions in said second region, and said inner edge portion and said outer edge portion carrying said first resealable adhesive in said second region are brought in contact with said adhesive-free edge portions at said first region;

wherein steps a-c are performed simultaneously; and wherein the one of said inner edge portion and said outer edge portion of said second edge zone of said first region that is provided with the first resealable adhesive is adjacent to said other of said inner edge portion and said outer edge portion of said second edge zone of said second region that is adhesive-free.

2. The method according to claim 1, wherein said method further comprises the step of:
g. releasably affixing a hygiene article to said user-facing surface of said release liner.

3. The method according to claim 2, wherein step g occurs before step e.

4. The method according to claim 2, further comprising the step of:
h. providing said user-facing surface of said release liner with a third resealable adhesive;
wherein step h occurs before step g.

5. The method according to claim 4, wherein said wrapping sheet has a first folding axis and a second folding axis dividing said wrapping sheet into said first region, said second region and a third region, said method further comprising the steps of:
i. providing a portion of an edge zone of said third region with said first resealable adhesive;
j. folding said wrapping sheet about said second folding axis such that an inner surface of said third region is brought in contact with an outer surface of said first region, wherein step i is performed simultaneously with steps a-c, and wherein step j is performed after step f.

6. The method according to claim 1, wherein said wrapping sheet is of substantially rectangular shape and comprises longitudinal edges, a first transverse edge and a second transverse edge and corner portions, said edge zones of said first region and said second region of said wrapping sheet being arranged along said longitudinal edges, and transverse edge zones arranged along said first transverse edge and said second transverse edge.

7. The method according to claim 6, said method further comprising the step of:
    k. providing at least one of said first transverse edge zone and said second transverse edge zone of said wrapping sheet with said first resealable adhesive.

8. The method according to claim 7, wherein step k is performed simultaneously with said steps a-c.

9. The method according to claim 6, wherein at least one of said corner portions is free from adhesive such that a gripping tab is formed.

10. The method according to claim 4, wherein said first resealable adhesive and said third resealable adhesive are pressure-sensitive hot melt adhesives, and said second adhesive is a construction adhesive.

11. The method according to claim 1, wherein said release liner is manufactured from one of paper, nonwoven and plastic film material.

12. The method according to claim 1, wherein said release liner is silicone-coated on said user-facing surface of said release liner.

13. The method according to claim 1, wherein a longitudinal extension of said release liner is 60-100% of a longitudinal extension of said wrapping sheet.

14. The method according to claim 1, wherein at least one of said wrapping sheet and said release liner is at least one of opaque and comprises print.

15. The method according to claim 1, wherein the one of said inner edge portion and said outer edge portion of said first edge zone in said first region that is provided with the first resealable adhesive is adjacent to said other of said inner edge portion and said outer edge portion of said first edge zone in said second region that is adhesive-free, and the other of said inner edge portion and said outer edge portion of said first edge zone in said first region that is adhesive-free is adjacent to said one of said inner edge portion and said outer edge portion of said first edge zone in said second region that is provided with the first resealable adhesive.

16. The method according to claim 1, wherein each wrapping sheet further comprises a second edge zone comprising an inner edge portion and an outer edge portion, and the method further comprises:
    providing one of said inner edge portion and said outer edge portion of said second edge zone of said first region with a first resealable adhesive, such that the other of said inner edge portion and said outer edge portion of said second edge zone of said first region is adhesive-free; and
    providing one of said inner edge portion and said outer edge portion of said second edge zone of said second region with a first resealable adhesive, such that the other of said inner edge portion and said outer edge portion of said second edge zone of said second region is adhesive-free in a complementary manner to said second edge zone of said first region; and
    the other of said inner edge portion and said outer edge portion of said second edge zone in said first region that is adhesive-free is adjacent to said one of said inner edge portion and said outer edge portion of said second edge zone in said second region that is provided with the first resealable adhesive.

17. The method according to claim 15, wherein each of the edge portions that are provided with adhesive extend along an entire length of its respective regions.

18. The method according to claim 16, wherein each of the edge portions that are provided with adhesive extend along an entire length of its respective regions.

* * * * *